(12) United States Patent
Merdan et al.

(10) Patent No.: US 6,764,710 B2
(45) Date of Patent: Jul. 20, 2004

(54) LIGHT EMITTING MARKERS FOR USE WITH SUBSTRATES

(75) Inventors: Kenneth M. Merdan, Greenfield, MN (US); Dachuan Yang, Plymouth, MN (US); Lixiao Wang, Long Lake, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 176 days.

(21) Appl. No.: 09/908,530

(22) Filed: Jul. 18, 2001

(65) Prior Publication Data

US 2003/0015284 A1 Jan. 23, 2003

(51) Int. Cl.[7] .................. A61L 27/00; A61L 29/06; B05D 3/06

(52) U.S. Cl. ............... 427/2.28; 427/2.1; 427/2.11; 427/2.29; 427/2.3; 427/2.31; 427/8; 427/9; 427/553; 156/60; 156/64; 156/67; 156/272.2; 156/272.8

(58) Field of Search .................. 427/2.1, 2.11, 427/2.28, 2.29, 2.3, 2.31, 8, 9, 553, 554, 557, 558, 372.2, 375; 156/60, 64, 67, 272.2, 272.8

(56) References Cited

U.S. PATENT DOCUMENTS

| | | | |
|---|---|---|---|
| 4,189,942 A | 2/1980 | Giezen et al. | 73/356 |
| 4,232,552 A | 11/1980 | Hof et al. | 73/356 |
| 4,251,305 A | 2/1981 | Becker et al. | 156/86 |
| 4,339,207 A | 7/1982 | Hof et al. | 374/160 |
| 4,362,645 A | 12/1982 | Hof et al. | 252/408.1 |
| 4,439,356 A | 3/1984 | Khanna et al. | 260/112 R |
| 4,452,720 A | 6/1984 | Harada et al. | 252/301.16 |
| 4,481,136 A | 11/1984 | Khanna et al. | 260/112 R |
| 4,749,585 A * | 6/1988 | Greco et al. | 428/422 |
| 5,066,580 A | 11/1991 | Lee | 435/721 |
| 5,115,136 A | 5/1992 | Tomasch | 250/461.1 |
| 5,188,934 A | 2/1993 | Menchen et al. | 435/6 |
| 5,227,487 A | 7/1993 | Haugland et al. | 546/15 |
| 5,231,191 A | 7/1993 | Woo et al. | 549/220 |
| 5,267,959 A | 12/1993 | Forman | 604/103 |
| 5,310,604 A | 5/1994 | Melancon et al. | 428/447 |
| 5,366,860 A | 11/1994 | Bergot et al. | 435/6 |
| 5,501,759 A | 3/1996 | Forman | 156/272.8 |
| 5,543,295 A | 8/1996 | Bronstein et al. | 435/6 |
| 5,654,442 A | 8/1997 | Menchen et al. | 549/223 |
| 5,662,712 A | 9/1997 | Pathak et al. | 623/12 |
| 5,667,840 A * | 9/1997 | Tingey et al. | 427/8 |
| 5,750,409 A | 5/1998 | Herrmann et al. | 436/517 |
| 5,782,180 A | 7/1998 | Schneider | |
| 5,807,605 A | 9/1998 | Tingey et al. | 427/8 |
| 5,840,999 A | 11/1998 | Benson et al. | 568/735 |
| 5,847,162 A | 12/1998 | Lee et al. | 549/227 |
| 5,936,087 A | 8/1999 | Benson et al. | 546/33 |

(List continued on next page.)

FOREIGN PATENT DOCUMENTS

| | | |
|---|---|---|
| EP | 0 682 145 A2 A3 | 5/1995 |
| EP | 0839634 | 6/1998 |
| FR | 1506163 | 12/1966 |
| WO | 97/32624 | 9/1997 |
| WO | 98/36707 | 8/1998 |
| WO | 99/16832 | 4/1999 |
| WO | 02/20881 | 3/2002 |

Primary Examiner—Shrive P. Beck
Assistant Examiner—Jennifer Kolb Michener
(74) Attorney, Agent, or Firm—Vidas, Arrett & Steinkraus

(57) ABSTRACT

A method of determining whether a substrate has been subjected to an energy source. In one embodiment, the method includes the steps of providing a polymeric surface, providing a light emitting material having a specified emission spectrum that changes upon exposure to an energy source on the surface or embedded in said substrate and applying said energy source to said surface with said light emitting material. This method can be particularly useful for detecting the bond quality in medical devices.

14 Claims, 5 Drawing Sheets

U.S. PATENT DOCUMENTS

| | | | |
|---|---|---|---|
| 6,013,728 A | 1/2000 | Chen et al. | 525/92 A |
| 6,025,505 A | 2/2000 | Lee et al. | 549/381 |
| 6,060,169 A | 5/2000 | Kuczynski et al. | 428/457 |
| 6,080,450 A | 6/2000 | Cantor | 427/517 |
| 6,080,852 A | 6/2000 | Lee et al. | 536/25.32 |
| 6,088,379 A | 7/2000 | Benson et al. | 549/224 |
| 6,139,525 A | 10/2000 | Davis-Lemessy et al. | 604/103 |
| 6,191,278 B1 | 2/2001 | Lee et al. | 546/41 |
| 6,242,063 B1 * | 6/2001 | Ferrera et al. | 428/35.2 |

* cited by examiner

LIGHT EMITTING MARKERS FOR USE WITH SUBSTRATES

FIELD OF THE INVENTION

The present invention relates to a method of determining if a material has been subjected to an energy source. More particularly, the present invention relates to methods which allow the inspection of one or more substrates to determine whether the substrate has been subjected to an energy source such as that used for welding or fusing of substrates. The invention includes the use of light emitting materials such as luminescent dyes and pigments such as a fluorescing agents, phosphorescing agents, visible dyes, or the like, which can be locally applied to the substrate.

BACKGROUND OF THE INVENTION

Medical devices such as catheter devices, are typically comprised of a number of components, some of which are sealed together using adhesives, thermal fusion, laser welding, and so forth.

Fusion, laser or thermal bonding are becoming more popular because the bonds typically achieved with these methods in contrast to adhesive bonds, are superior in strength. Furthermore, the use of adhesives adds to the thickness of the catheter and increases the rigidity at the region of the bonds.

It is of significant importance in the manufacture of catheter devices to be able to achieve a good seal when bonding the various components together regardless of the method used. This is, however, often a difficult task due to the very small size of these medical devices.

One such method of monitoring the performance of the bond or seal achieved, is to use tensile and burst testing. However, this involves the destruction of the substrates.

For laser and thermal welding, the surface of the material may change, in some cases, from a shiny to a matte finish. It has been hypothesized that this may be indicative of the bond strength. However, tensile and burst testing are still required to ultimately determine bond performance.

Providing a bond through fusion or laser welding of materials including polymeric and metallic materials, is becoming a popular alternative to adhesive usage. It is also, consequently, desirable to have a method by which bonds can be inspected and performance ascertained without destroying the bonded substrates because destruction of the substrates can be of detriment economically, and in any event, waste is undesirable.

Luminescent (including fluorescent and phosphorescent) markers have been used for a wide variety of applications in science, medicine and engineering. For instance, the incorporation of fluorescent compounds into coating compositions is known. For example, the addition of fluorescing agents to coatings is now used to determine thickness of release coatings. Fluorescing agents added to coatings will emit radiation of an intensity that is proportional to the coating thickness. Sensors can then be used to produce an electronic signal proportional to the emission intensity. Further, a controller may be installed on manufacturing equipment to which uses this signal to make mechanical adjustments to the coating machine in order to maintain constant coating thickness.

U.S. Pat. No. 5,310,604 describes a method for monitoring the coating weight, uniformity, defects or markings present in a coating of a composition applied to a substrate by using an effective amount of a uv-escer in the coating composition.

U.S. Pat. No. 6,060,169 describes a material and a method for forming a tamper-indicating identification coating.

U.S. Pat. No. 6,080,450 describes the incorporation of a high concentration of luminescing agent, e.g. fluorescing agent, into an actinic radiation, e.g. UV, curable polymerizable acrylate formulation using a phosphine oxide photoinitiator to enable the curing, the luminescing or fluorescing agent present to facilitate and enhance the efficiency of evaluation of the cured deposit by utilizing its fluorescent response.

Furthermore, the incorporation of fluorescent compounds into coating compositions to provide a non-destructive method for inspection of the quality, consistency, and so forth of the coating is discussed in U.S. Pat. Nos. 6,080,450 and in 5,310,604.

There remains a need in the art, however, for an easy method of monitoring and inspecting a bond or seal formed by thermal fusion or laser welding.

SUMMARY OF THE INVENTION

The present invention allows for determination of whether or not a source of energy has been applied to a substrate. The present invention relates to a method of manufacturing a medical device including the steps of selecting a first substrate, selecting a light emitting material having a first emission spectrum and a second emission spectrum different from said first emission spectrum upon subjection to a source of energy, applying the light emitting material to a polymeric substrate, and applying a predetermined energy source to the substrate sufficient to change the first emission spectrum of the light emitting material to the second emission spectrum. The second emission spectrum may constitute a non-emission.

The method can also include the step of detecting the second emission spectrum on the substrate. The second detected emission spectrum may be utilized to indicate the receipt by the substrate of a predetermined energy dosage. The first substrate may be joined to a second substrate before applying the predetermined energy source.

In one embodiment of the present invention, the predetermined level of energy applied may be that required to alter the physical properties of the polymeric substrate(s).

In another aspect, the present invention allows for non-destructive observation of a joint between a polymeric substrate and a second substrate such as in the case where the substrates have been joined by fusion or welding.

The present invention, in another aspect, can provide a method of detecting the optimal temperature for welding or fusing a first substrate and a second substrate, at least one of which is polymeric. The method includes the steps of providing a first substrate and second substrate of the same or a different material wherein at least one of the first, the second substrate, or both, is polymeric. The light emitting material of the present invention is applied to the substrate is applied to the substrate at a location where the first substrate and the second substrate will be joined. The light emitting material has a first emission spectrum that changes to a second, different emission spectrum upon exposure to a predetermined energy source. The first and second substrates may be joined by welding or fusing.

The light emitting material is selected so that the first emission spectrum of the light emitting material changes to the second emission spectrum when the predetermined source of energy required for welding has been supplied to the welding site. The predetermined source of energy may be a specified temperature, or it may be a specified wavelength, and so forth. In laser welding, for instance, at a given wavelength, the polymeric substrate is actually heated to a temperature that allows for welding.

In this aspect of the invention, the method allows for a means of detecting when the temperature for welding various polymeric materials has been achieved by incorporation of a light emitting material composition with a known emission spectrum at the interface of the bond. The light emitting material composition will emit energy of a given wavelength when exposed to a particular predetermined source of energy.

In one particular embodiment of the present invention, the light emitting material emits energy in the fluorescent region. Upon application of a predetermined energy source, the first emission spectrum of the light emitting material changes to the second emission spectrum. This change may be a shift from one fluorescent emission spectrum to another fluorescent emission spectrum, or the light emitting material may stop fluorescing altogether.

For instance, a fluorescent dye may be selected wherein the first fluorescent emission spectrum changes upon exposure to a source of energy that heats the substrate such as thermal energy, or a laser. The first fluorescent emission spectrum changes to a second emission spectrum upon achieving temperatures in excess of 100° C. This change may be in the fluorescent range, or the second emission spectrum may be in a different wavelength range altogether.

In the case of thermal welding applications, for instance, the light emitting material may be selected based on the melting temperature of the polymeric substrate being welded, as well as to the predetermined energy source. In this instance, the emission spectrum of the light emitting material will desirably change at a temperature that is at or above the melting temperature of the polymer, for instance. Optionally, the light emitting material may respond and its emission spectrum change at the wavelength at which a laser is applied to weld the polymeric substrate(s).

The light emitting material thus responds to different wavelengths of energy supplied, or to different temperatures, for instance.

In this embodiment, the method of the present invention therefore allows for easy visual or instrumental inspection of welded joints. The areas that are exposed to the desired temperature or wavelength, for example infrared, ultraviolet, and so forth, will respond by a change in the emission spectrum or color of the light emitting material, indicating that the joint has reached the temperature or wavelength for an optimum seal.

The method of the present invention finds particular utility in the medical device art, in particular for intraluminal medical devices such as catheter delivery devices.

It is of importance in the manufacture of medical devices, in particular catheter delivery devices, that good seals between parts are achieved. For instance, when bonding a dilatation balloon to a catheter tube or shaft, if a tight seal is not achieved, inflation fluid may leak from the seal, and the desired pressure for inflation may not be achievable. The present invention therefore provides an easy and efficient way of monitoring the quality of the seal.

DETAILED DESCRIPTION OF THE PREFERRED EMBODIMENTS

Figure 1A:
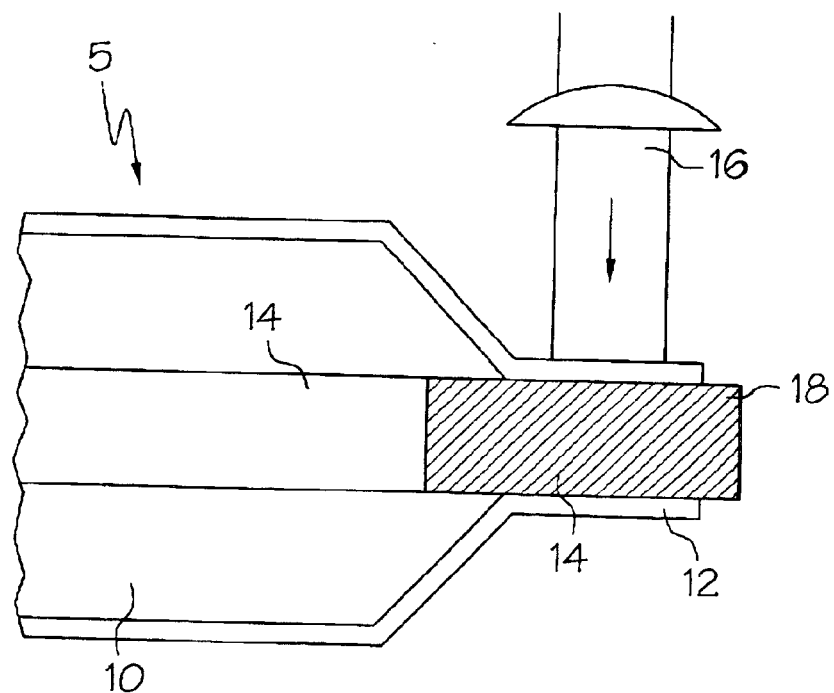
FIGS. 1A and 1B are cross-sectional illustrations of a catheter balloon mounted on a catheter shaft before and after laser welding the balloon to the shaft.

While this invention may be embodied in many different forms, there are described in detail herein specific embodiments of the invention. This description is an exemplification of the principles of the invention and is not intended to limit the invention to the particular embodiments illustrated.

At least one polymeric substrate is utilized in manufacturing the medical devices of the present invention. Suitable generic classes of polymers include, but are not limited to, thermoplastic polyurethanes, polyamides, nylons, polyesters, polyolefins, polyvinyl chloride, thermoplastic polyurethanes, polyimides, and their copolymers, terpolymers, and so forth, thereof. The term copolymer will hereinafter be used to refer to those polymers having two or more different monomers as well as two.

Even more specific exemplary polymers include, but are not limited to, polyethyleneterephthalate (PET); the HYTREL® family of polyester elastomers available from DuPont in Wilmington, Del.; the PEBAX® family of block copolymers which are more specifically polyether-block-amide copolymers available from Elf Atochem North America, Inc. in Philadelphia, Pa.; and the TECOTHANE® family of aromatic, polyether based thermoplastic polyurethanes available from Thermedics Polymer Products, a division of Thermo Electron Corp. in Woburn, Mass.

The light emitting materials useful herein include luminescent such as fluorescent and phosphorescent materials, and colored (i.e. in the visible range) dyes and pigments, and have the characteristic that they are "light emitting" which as defined herein as those materials that absorb and re-emit light. Therefore, for purposes of this specification, "light emitting material" will also be used to refer to those materials whose emission spectrum might include transmission or reflection.

Generally, the light emitting materials useful herein have first predetermined and specific emission spectra that change to a second predetermined and specific emission spectra upon exposure to a predetermined energy source. The change in emission occurs upon exposure to a preselected energy source in a predictable manner. In most instances, the change in the emission spectrum will be a permanent change, although some light emitting materials may exhibit a reversible change in emission. The change in emission may reflect a chemical change in the light emitting material.

Some of the agents or light emitting materials suitable for use herein are those that emit light in the frequency range of about 200 nm to about 1100 nm, including the ultraviolet/visible (UV/Vis) range. The visible range is greater than about 500 nm.

Fluorescent dyes absorb light at wavelengths of about 250 nm to about 450 nm, and have the characteristic that they absorb a photon of radiant energy at a particular wavelength and then quickly re-emit the energy at a slightly longer wavelength. For instance, fluorescent compounds may absorb ultraviolet (UV) light, (such as from daylight) at 300–430 nm and re-emit most of the absorbed energy as blue fluorescent light between 400 and 500 nm. However, fluorescent compounds can refer to any molecule which absorbs light of wavelengths of 250 nm to 1100 nm and which emits light by either fluorescence or phosphorescence, or both. Fluorescent dyes are typically colorless to weakly colored organic compounds that, in solution, or, when applied to a substrate impart little color to the substrate, a characteristic that is particularly desirable for most, but not all applications, in the medical device industry.

Some common classes of fluorescent dyes include, but are not limited to, xanthenes such as rhodamine and fluorescein; bimanes; coumarins such as umbelliferone; aromatic amines such as dansyl; squarate dyes; benzofurans; cyanines, merocyanines; rare earth chelates; carbazoles; and the like.

More specific examples of fluorescent dyes suitable for use herein include, but are not limited to, benzenes such as distyryl benzenes; phenyl and phenyl derivatives; biphenyls such as 4,4'-distyryl-biphenyls; stilbenes and stilbene derivatives such as divinyl stilbenes, triazinyl amino stilbenes, bis(1,2,3-triazol-2-yl) stilbenes; stilbenzyl-2H-triazoles such as stilbenzyl-sH-naphtho[1,2-d] triazoles; benzoxazole and benzoxazole derivatives such as such as stilbenzylbenzoxazoles and bis(benzoxazoles); furans ans benzo[b] furans such as bis(benzo[b] furan-2-yl) biphenyls; benzimidazoles such as cationic benzimidazoles; 1,3-diphenyl-2-pyrazolines; naphthalimides and 1,3,5-triazin-2-yl derivatives; naphthalene and naphthalene derivatives such as 5-dimethylaminonaphthalene-1-sulfonic acid and N,N-dimethylamino-5-propionylnaphthalene; hydroxy naphthalenes; anthracene and anthracene derivatives such as 9,10-diphenylanthracene, 9-methylanthracene, 9-anthracene carboxaldehyde, anthryl alcohols and 9-phenylanthracene; xanthenes such as rhodamine and rhodamine derivatives such as rhodols, tetramethyl rhodamine, tetraethyl rhodamine, diphenyldimethyl rhodamine, diphenyldiethyl rhodamine and dinaphthyl rhodamine; xanthenes such as fluorescein and fluorescein derivatives such as 5-iodoacetamido fluorescein, 6-iodoacetamido fluorescein and fluorescein-5-maleimide; coumarin and coumarin derivatives such as the aminomethyl coumarins including 7-dialkylamino-4-methylcoumarin, 4-bromomethyl-7-methoxycoumarin and 4-bromomethyl-7-hydroxy coumarin; erythrosin and erythrosin derivatives such as hydroxy erythrosins, erythrosin-5-iodoacetamide and erythrosin-5-maleimide; acridine and acridine derivatives such as hydroxy acridines and 9-methyl acridine; pyrene and pyrene derivatives such as N-(1-pyrene) iodoacetamide, hydroxy pyrenes and 1-pyrenemethyl iodoacetate, pyrenyloxy sulfonic acids and pyrenes with aminocoumarin conjugates, in particular dialkylaminocoumarin pyrenes; stilbene and stilbene derivatives such as 6,6'-dibromostilbene and hydroxy stilbenes; nitrobenzoxadiazoles and nitrobenzoxadiazole derivatives such as hydroxy nitrobenzoxadiazoles, 4-chloro-7-nitrobenz-2-oxa-1,3-diazole, 2-(7-nitrobenz-2-oxa-1,3-diazole-4-yl)methylaminoacetaldehyde and 6-(7'-nitrobenz-2-oxa-1,3-diazole-4-yl)aminohexanoic acid; quinoline and quinoline derivatives such as 6-hydroxyquinoline and 6-aminoquinoline; acridine and acridine derivatives such as N-methylacridine and N-phenylacridine; acidoacridine and acidoacridine derivatives such as 9-methylacidoacridine and hydroxy-9-methylacidoacridine; carbazole and carbazole derivatives such as N-methylcarbazole and hydroxy-N-methylcarbazole; fluorescent cyanines such as DCM (a laser dye), hydroxy cyanines, 1,6-diphenyl-1,3,5-hexatriene, 1-(4-dimethyl aminophenyl)-6-phenylhexatriene and the corresponding 1,3-butadienes; carbocyanines and carbocyanine derivatives, such as phenylcarbocyanine and hydroxy carbocyanines; pyridinium salts such as 4(4-dialkyldiaminostyryl)-N-methyl pyridinium iodate and hydroxy-substituted pyridinium salts; oxonols; and resorofins and hydroxy resorofins; xanthene and xanthene derivatives such as benzothioxanthene and benzoxanthene; naphthalimides; 1,3,5-triazin-2-yl derivatives; and so forth.

Suitable fluorescent dyes are discussed in Ullman's Encyclopedia of Industrial Chemistry Vol. A18 (5th Edition) pp. 153–167 incorporated by reference herein and in U.S. Pat. No. 5,543,295 incorporated by reference herein. Further suitable fluorescent materials suitable for use in the compositions herein are detailed in EP Application No. EP 682145 in the name of CIBA-GEIGY AG, the contents of which are incorporated herein by reference in their entirety.

One specific example of a particularly useful fluorescent dye includes 3,3'-bis-(3-sulfopropyl-5,5'-dichloro-9-cetylthiacarbocyanine which exhibits a five-fold decrease in its 625/550 nm absorbtion ratio when the temperature exceeds room temperature.

Examples of commercially available fluorescent dyes include CASCADE BLUE®, a pyrenyloxy sulfonic acid available from Molecular Probes, Inc. in Eugene, Oreg.; FLUORESCEIN® (dye content~95%) and FLUORESCENT BRIGHTENER 28 FREE ACID fluorescent dye, both available from Sigma-Aldrich Corp., benzoxazoles derivatives such as Uvitex® OB (bis-benzoxazolyl) available from Ciba Specialty Chemicals in Basel, Switzerland; Blankophor® CA 4410 available from Bayer Corp. in Pittsburgh, Pa. (parent company is Bayer AG in Germany); Fibers, Additives and Rubber Division; such as ALEXA FLUOR® 350 (carboxylic acid succinimidyl ester) and AMCA-X Dyes (succinimidyl ester); succinimidyl ester mixed isomers (i.e. of sulforhodamine 101) such as RHODAMINE RED® (or TEXAS RED-X®) available from Molecular Probes, Inc. in Eugene, Oreg.; and so forth. Mixtures of the fluorescing agents are also useful herein.

UVITEX® fluorescing agents, benzoxazole derivatives, are commercially available from Ciba Specialty Chemicals in Tarrytown, N.Y. UVITEX® OB, a 2,5-(di-5tert-butylbenzoyl)thiophenate, is a specific example of a commercially available fluorescing agent available from Ciba Specialty Chemicals.

Other useful commercially available fluorescing agents include other benzoxazole derivatives such as HASTA-LUX® KCB, a 2,2-(1,4-Naphthalenediyl)bis-benzoxazole; and the EASTOBRITE® line available from Eastman Chemical Co. in Kingsport, Tenn., including EASTOBRITE® OB-1, a 2,2'-(1,2-ethenediyldi-4,1-phenylene) bisbenzoxazole.

Yet other useful commercially available fluorescent suitable for use herein include, for example, Basic Yellow 40, Basic Red 1 xanthene dye (rhodamine), Basic Violet 11 xanthene dye (rhodamine), Basic Violet 10, Basic Violet 16, Acid Yellow 73, Acid Yellow 184, Acid Red 50, Acid Red 52, Solvent Yellow 44, Solvent Yellow 131.

Phosphorescent compounds or phosphors are substances that emit light after having absorbed ultraviolet radiation or the like, and in contrast to fluorescent compounds, the afterglow of the light that can be visually observed continues for a considerable time, ranging from several tens of minutes to several hours after the source of the stimulus is cut off.

Examples of phosphorescent compounds suitable for use herein include, but are not limited to, porphyrins, phthalocyanines, polyaromatic compounds such as pyrene, anthracene and acenaphthene. Many phosphors are inorganic solids prepared from a metal cation, a nonmetal anion and an activator. The activator is usually a transition or a rare earth element which when added in small amounts (0.1% to 5%) can alter the color of the emitted light. Halogenation of some fluorescent dyes leads to phosphorescence. For instance, the polybrominated and polyiodinated analogs of fluorescein dyes have much lower fluorescence yields, and higher phosphorescence yields.

Colored dyes (exhibit color in the visible range) useful herein include, but are not limited to, indoaniline dyes, indophenol dyes, quinone monoimine dyes, quinone diimine dyes, cyanine dyes, merocyanine dyes, cyclohexadienone dyes, iminocyclohexadienone dyes, imidazolylidinecyclohexadienone dyes, dihydronaphthalenone dyes, iminodihydronaphthalenone dyes, imidazolylidinedihydronaphthalenone dyes, cyclohexadienimine dyes, aryl substituted bis trifluoromethylsulfonylhexatrienyl dyes, aryl substituted bis (trifluoromethylsulfonyl)butadienyl dyes, aryl substituted bis (fluorosulfonyl)hexatrienyl dyes, aryl substituted bis (fluorosulfonyl)butadienyl dyes, oxazolone dyes, cationic dyes, anionic dyes, amphoteric dyes, and so forth.

More specific examples of such dyes include, but are not limited to, 4-[[4-(Dimethylamino)phenyl]imino]-2,5-cyclohexadien-1-one; 2-Chloro-4-[[2-methyl-4-(diethylamino)phenyl]imino]-2,5-cyclohexadien-1-one; 4-[[4-(Diethylamino)phenyl]imino]-1,4-dihydronaphthalen-1-one; 4-[[4-(Dimethylamino)phenyl]imino]-1,4-dihydronaphthalen-1-one; 4-[[2-methyl-4-(diethylamino)phenyl]imino]-1,4-dihydronaphthalen-1-one; 3-Methoxy-4-[[2-methyl-4-(diethylamino)phenyl]imino]-2,5-cyclohexadien-1-one; 3-Chloro-4-[[2-methyl-4-(diethylamino)phenyl]imino]-2,5-cyclohexadien-1-one; 2-Methyl-4-[[4-(4-morpholinyl)phenyl]-imino]-2,5-cyclohexadien-1-one; 2,6-Dichloro-4-[[4-(4-morpholinyl)-phenyl]imino]-2,5-cyclohexadien-1-one; 2,6-Dimethyl-4-[[4-(4-morpholinyl)-phenyl]imino]-2,5-cyclohexadien-1-one; 2,5-Dichloro-4-[[4-(diethylamino)-phenyl]imino]-2,5-cyclohexadien-1-one; 3-Methoxy-4-[[3-methoxy-4-(diethyl-amino)phenyl]imino]-2,5-cyclohexadien-1-one; 2,6-Di chloro-4-[[2-methyl-4-(diethylamino)phenyl]imino]-2,5-cyclohexadien-1-one; 3-[[4-(Diethylamino)-2-methylphenyl]imino]-6-oxo-N-phenyl-1,4-cyclohexadiene-1-carboxamide; 5-[[4-(Diethylamino)-2-methylphenyl]imino]-8-(5H)-quinolinone; 2,5-Dichloro-4-[[2-methyl -4-(diethylamino)-phenyl]imino]-2,5-cyclohexadiene-1-one; 2,6-Dichloro-4-[[4-(acetamido)phenyl]imino]-2,5-cyclohexadiene-1-one; 2,6-Dichloro-4-[4-ethoxy phenyl)imino]-2,5-cyclohexadien-1-one; 2,6-Dichloro-4-[(2-methyl-4-ethoxy phenyl)imino]-2,5-cyclohexadien-1-one; 2,6-Dimethyl-4-[4-hydroxy phenyl)imino]-2,5-cyclohexadien-1-one; 2,6-Dichloro-4-[(4-methoxy-1-naphthyl)imino]-2,5-cyclohexadien-1-one; 2,6-Dichloro-4-[[4-(benzyloxy)phenyl]imino]-2,5-cyclohexadien -1-one; 2,6-Dichloro-4-[(2,4-dimethoxyphenyl)imino]-2,5-cyclohexadien-1-one; 2,6-Dichloro-4-[(4-methoxyphenyl)imino]-2,5-cyclohexadien-1-one; 4-(phenylimino)-2,5-cyclohexadien-1-one; 4-(1-naphthylimino)-2,5-cyclohexadien-1-one; 4-(2-naphthylimino)-2,5-cyclohexadien-1-one; 2,5-Bis(phenylamino)-4 (phenylimino)-2,5-cyclohexadien-1-one; 2,5-Dibromo-4-[(2,4-dibromophenyl)imino]-2,5-cyclohexadien-1-one; 2,3,5-Trichloro-4-[(2,4,6-trichlorophenyl)imino]-2,5-cyclohexadien-1-one; 2,6-Dichloro-4-[4-[4-(dimethylamino)phenyl]-5-phenyl-(2H)-imidazol-2-ylidine]-2,5-cyclohexadien-1-one; 2,6-Dichloro-4-[4,5-bis (4-hydroxyphenyl)-(2H)-imidazol-2-ylidine]-2,5-cyclohexadien-1-one; 2,6-Dimethoxy-4-[4,5-bis(2-furyl)-(2H)-imidazol-2-ylidine]-2,5-cyclohexadien-1-one; 2,6-Bis [1,1-(dimethyl)ethyl]-4-[4,5-bis(2-furyl)-(2H)-imidazol -2-ylidene]-2,5-cyclohexadien-1-one; 4-(phenylimino)-2,5-cyclohexadien-1-imine; Mono[(3-methyl-2-(3H)-benzothiazolylidene)hydrazono]2,5-cyclohexadiene-1,4-dione; 4-[(3-Chloro-4-oxo-2,5-cyclohexadien-1-ylidene)-amino]-1,2-dihydro-1,5-dim ethyl-2-phenyl-(3H)-pyrazol-3-one; 4-[(3,5-Dichloro-4-oxo-2,5-cyclohexadiene-1-ylidene)amino]-1,2-dihydro-1,5-dimethyl-2-phenyl-(3H)-pyrazol-3-one; 3-[(3,5-Dichloro-4-oxo-2,5-cyclohexadien-1-ylidene)amino]-2,5-dihydro-4,5-dimethyl-1-phenylpyrrol-2-one; 4-(Phenylsulfonyl)imino-1-[4-[(phenylsulfonyl) imino]-2,5-cyclohexadien-1-y lidenyl]-2,5-cyclohexadiene; 4-[6,6-Bis[(trifluoromethyl)sulfonyl]-1,3,5-hexatrienyl]-N, N-dimethylbenze namine; 4-[4,4-Bis[(trifluoromethyl) sulfonyl]-1,3-butadienyl]-2-ethoxy-N,N-dimethy lbenzenamine; 4-[4,4-Bis[(trifluoromethyl)sulfonyl]-1,3-butadienyl]-2,5-dimethoxy-N,N-di methylbenzenamine; 9-[4,4-Bis[(trifluoromethyl)sulfonyl]-1,3-butadienyl]-2,3,6,7-tetrahydro-(1H,5H)-benzo[ij]quinolizine; 4-[4,4-Bis [(trifluoromethyl)sulfonyl]-1,3-butadienyl]-2,6-N,N-tetramethyl-benzenamine; 4-[5,5-Bis[(trifluoromethyl) sulfonyl]-2,4-pentadienylidene]-1,4-dihydro-1-methylquinoline; 6,6-Bis[4-(dimethylamino)phenyl]1,3,5-hexatriene-1,1-bis(sulfonylfluoride); 4-[4,4-Bis [(trifluoromethyl)sulfonyl]-1,3-butadienyl]-N,N-dimethylbenzena mine; and 4-[3-[4-(Dimethylamino) phenyl]-2-propenylidene]-2-phenyl-5(4H)-oxazolone; anionic dyes having the following anions: 5-[5-(1,3-Diethylhexahydro-2,4,6-trioxo-5-pyrimidinyl)-2,4-pentadieniden e]-1,3-diethyl -2,4,6(1H,3H,5H)-pyrimidenetrione; and cationic dyes having the following cations or having the cations of the following cationic dyes: 3H-Indolium, 3-[3-[4-(dimethylamino)phenyl]-2-propenylidene]-1-methyl-2-phenyl; Benzothiazolium, 3-(3-amino-3-oxopropyl)-2-[[4-[bis(2-chloroethyl)amino] phenyl]azo]-6-metho xy-; Benzothiazolium, 3-(3-amino-3-oxopropyl)-2-[[4-(diethylamino)phenyl]azo]-6-ethoxy-; Benzothiazolium, 3-(3-amino-3-oxopropyl)-2-[[4-(diethylamino)-2-methylphenyl]azo]6-ethoxy-; C.I. Basic Blue 68; C.I. Basic Blue 76; C.I. Basic Blue 57; C.I. Basic Blue 60; Benzo[a]phenoxazin-7-ium, 9-(dimethylamino)-; 2-[4,4,-bis[4-dimethylamino)phenyl]-1,3-butadienyl]-1-ethyl quinolinium; 4-[4,4,-bis[4-(dimethylamino)phenyl]-1,3-butadienyl]1-ethyl quinolinium; Naphtho[2,1-d] thiazolium, 2-[4,4-bis[4-(dimethylamino)phenyl]-1,3-butadienyl]-3-ethyl-; 2-[2-[4-(dimethylamino)phenyl] ethenyl]-1-phenyl-3-methyl quinoxalinium; Quinolinium, 2-[3-(5-chloro-1,3-dihydro-1,3,3-trimethyl-(2H)-indol-2-ylidene)-1-propeny l]-1-methyl-; Benzothiazolium, 2-[[4-(dimethylamino)phenyl]azo]-6-methoxy-3-methyl-; Benz [cd]indolium, 2-[4-(diethylamino)-2-ethoxyphenyl]-1-ethyl-; 2-[p-(Dimethylamino)styryl]-1,3-dimethylquinoxalinium; 2-[3-(5-chloro-1,3-dihydro-1,3,3-trimethyl-(2H)-indol-2-ylidene)-1-propeny l]-1-methylquinoxalinium; C.I. Basic Blue 40; Benzothiazolium, 2-[[4-[ethyl(2-hydroxyethyl)amino]phenyl]azo]-6-methoxy-3-methyl-; Benzothiazolium, 2-[[4-[ethyl(2-hydroxyethyl)amino]phenyl]azo]-6-methoxy -3-methyl-; C.I. Basic Blue 42; C.I. Basic Blue 53; 3H-Indolium, 5-chloro-2-[5-(5-chloro-1,3-dihydro-1,3,3-trimethyl-2H-indol-2-ylidene)-1,3-pentadienyl]-1,3,3-trimethyl-; Basic Blue 142; Benz[cd]indolium, 2-[2-(9-ethyl-(9H)-carbazol-3-yl)ethenyl]-1-methyl-; Benz[cd]indolium, 2-[2-[4-(dimethylamino)phenyl]-2-phenylethenyl]-1-methyl-; Benz

[cd]indolium, 2-[2,2-bis[4-(dimethylamino)phenyl] ethenyl]-1-methyl-; Benz[cd]indolium, 2-[2-(2,3-dihydro-1-methyl-2-phenyl-1H-indol-3-yl)-2-(2-methylphenyl)etheny l]-1-methyl-; Pyrimidinium, 4-[5-(2,3-dihydro-1,3-dimethyl-2-oxo-; 4(1H)-pyrimidinylidene)-1,3-pentadienyl]-2,3-dihydro-1,3-dimethyl-2-oxo-; 3H-Indolium, 2-[[3-[(1,3-dihydro-1,3,3-trimethyl-2H-indol-2-ylidene)methyl]-5,5-dimethy 1-2-cyclohexen-1-ylidene] methyl]-1,3,3-trimethyl-; Benz[cd]indolium, 2-[2-[4-(diethylamino)-2-methylphenyl]ethenyl]-1-methyl-; 3H-Indolium, 3-[3-[4-[(dimethylamino)phenyl]-2-propenylidene]-1-methyl-2-(4-methoxyphen yl)-; 3H-Indolium, 3-[(2,5-dimethyl-1-phenyl-(1H)-pyrrol-3-yl) methylene]-1,2-dimethyl-; 3H-Indolium, 3-[2,5-dimethyl-1-phenyl-(1H)-pyrrol-3-yl)methylene]-1-methyl-2-phenyl-; 2-[2-[2-chloro-4-(dimethylamino)phenyl]ethenyl]-1-methylbenz[cd]indolium; C.I. Basic Violet 22; C.I. Basic Red 15; Benz[cd]indolium, 2-[2-[4-(dimethylamino)phenyl] ethenyl]-1-methyl-; Benz[cd]indolium,2-[2-[4-(dimethylamino)-2-ethoxyphenyl]ethenyl]-1-methyl-; and 3H-Indolium, 2-[1-cyano-4,4-bis[4-(dimethylamino) phenyl]-1,3-butadienyl]-1,3,3-trimethy 1-.

The above dyes are described for use in temperature indicating devices in U.S. Pat. Nos. 4,339,207, U.S. 4,362, 645 and U.S. 4,232,552 each of which is incorporated by reference herein in their entirety. Dyes useful herein are also described in U.S. Pat. No. 4,189,942 which is incorporated by reference herein in its entirety.

Advantageously for medical device manufacture, but not necessarily, the light emitting materials are biocompatible materials. Examples of some biocompatible dyes include ethanol-based COOMASSIE® Brilliant Blue dyes such as R-250, riboflavin, RHODAMINE® dyes, methylene dyes, and so forth.

One of skill in the art would recognize that there is an endless selection of light emitting materials available for use herein. Those described above are for exemplary purposes only. The light emitting materials may be substituted with others not listed without deviating from the scope or intent of the present invention.

The energy sources suitable for use herein include, but are not limited to, laser, infrared and ultraviolet heat sources, thermal energy sources, microwave, x-ray, nuclear radiation such as gamma radiation, ultrasonic, radio frequency (Rf), and so forth. These are intended for exemplary purposes only and not as an exhaustive list of possible energy sources useful herein.

Laser energy may be further classified as solid state, infrared, free electron laser, gas discharge, visible light, ultraviolet, Rf, and so forth.

The near infrared and infrared lasers, including solid state infrared lasers, suitable for use herein include those those having wavelengths from about 0.7 to about 2.0 micrometers within the near-IR, or wavelengths from about 4.0 to about 6.0 micrometers within the IR. Examples of such lasers include solid-state YAG lasers including neodymium-doped yttrium aluminum garnet lasers which emit at about 2 to about 3 micrometers in wavelength and their harmonics at shorter wavelengths, diode lasers including erbium-glass and semiconductor aluminum gallium arsenide lasers, and carbon monoxide (CO) lasers which emit at about 5 to about 6 micrometers in wavelength, hydrogen-fluoride (HF) which emit at about 2 to 3 micrometers in wavelength, and so forth. Other lasers operating in the infrared region include Rf (radio-frequency discharge) $CO_2$ lasers or TEA (transverse electric discharge-atmospheric pressure) $CO_2$ lasers, and the like.

Both YAG lasers and $CO_2$ lasers transform optical energy to thermal energy. Material can thus be heated to melt or vaporize and is thus taken the material from solid state to liquid or gaseous state with these lasers.

Such energy source can operate at wavelengths between about 2 microns and about 12 microns.

Lasers operating in the ultraviolet region may be further classified as solid states lasers or excimer lasers. Excimer lasers include, but are not limited to, free electron lasers, gas discharge lasers, and copper vapor lasers. Typical excimer lasers include, but are not limited to, argon ion (Ar) lasers, krypton (Kr) ion lasers, helium-neon(He—Ne), KrF (krypton fluoride), XeF (xenon fluoride), XeCl (xenon chloride), KrCl (krypton chloride), ArF (argon fluoride) lasers, and so forth.

Lasers operating in the visible region include helium-neon (He—Ne) lasers. He—Ne lasers operate at a wavelengths of about 630–635 nm.

Excimer layers, in contrast to Nd:YAG and $CO_2$ lasers do not generate thermal energy and are referred to as "cold cutting lasers". Excimer lasers can be said to operate by direct solid-vapor ablation. The incident photon energy is high enough to break the chemical bonds of the target material directly, the material is dissociated into its chemical components, and no liquid phase transition occurs in this process. This chemical dissociation process has much minimized heat effects compared with the physical phase change process. UV laser is capable of ablating organic compounds. Heat generation is thus neglected. Excimer lasers can cause crosslinking in polymeric materials.

The light emitting agent may be applied to the substrate in any way conventionally known. For instance, the light emitting agent may be painted, sprayed, or otherwise coated on the surface of the polymeric substrate. The light emitting material may also be embedded in the surface of the polymeric substrate, or it may be blended into the polymeric composition prior to further processing of the polymeric composition into a shaped substrate. This may involve melt or solution blending of the polymer with the light emitting material. In instances where it is desirable to have the light emitting material only on particular areas of the substrate, blending with the polymer may not be a satisfactory option.

The light emitting agent, if in solid form, may be dissolved into solution for application to the polymeric substrate surface in instances where it is desirable to paint, spray or otherwise coat it on the surface of a substrate. Solvents useful herein include water and organic solvents including both polar and nonpolar type solvents such as alcohols including isopropanol and ethanol, chlorinated solvents, esters, glycols, glycol ethers, ketones, aliphatic hydrocarbons including heptane and hexane, aromatic hydrocarbons, and so forth. The selection of a solvent will be based not only on the solubility of the fluorescing agent in the solvent, but also on the solvents affect on the polymer substrate, and low toxicity.

The energy source is then applied to the polymeric substrate. The light emitting material will be selected so as to absorb the energy at wavelengths where the energy source operates. For instance, if a laser is the energy source utilized, and it operates at wavelengths of about 400 nm, a fluorescent dye may be selected which will absorb energy at 400 nm and re-emit light at a slightly longer wavelength of perhaps 450–500 nm. The light emitting material will also be chosen such that its emission spectrum will change upon absorption by the substrate of a specified amount of energy. The change in emission may indicate a chemical, physical or some such change by the light emitting material, and indicates that the predetermined energy source has been applied to the substrate. The change in emission may also indicate a physical or chemical change in the substrate material itself. It is desirable that these changes coincide with one another such that the light emitting material is indicative not only of changes in itself, but also that the energy source has been applied in the requisite amount, and also of the changes in the substrate if so desired.

The present invention therefore finds utility in indicating a change in a polymeric substrate upon application of an energy source thus indicating that the energy source has been applied. The change in the substrate may be chemical, physical, or some such other change.

The change in emission of the dye may be a simple shift from one spectrum to the next but remaining in the same range, or it may be a shift from one range to another, or the dye may stop emission altogether, for instance, becoming opaque.

Useful detection methods include observation with the naked eye if the light emitting material emits light in the visible range, or with an instrument. Useful detection methods include, but are not limited to, ultraviolet light detection, electron beam detection, and so forth.

While the present invention can therefore be utilized on a single substrate, it finds particular utility in instances where it is desirable to join a first substrate with a second substrate, such as in article assembly, through the use of thermal or radiant, i.e. excitation energy. The second substrate may be polymeric in nature, or it may also be a metal or metal alloy, or some other substrate such as glass or ceramic. If the second substrate is polymeric in nature, it may be of the same polymeric composition as the first substrate, or it may be of a different polymeric composition. Furthermore, either of the first substrate, the second substrate, or both, may be comprised of a single polymeric material, a blend of polymers, or a blend of polymer(s) as well as other materials such as plasticizing materials, for instance.

In this embodiment, the light emitting material may be applied to at least one of the substrates using any standard method of application known in the art as described above. However, in this embodiment, it may be preferable to apply or embed the light emitting material at or around the interface of the site where the substrates are to be joined only. Blending the light emitting material in the polymeric composition prior to substrate formation will not allow for a controlled placement of the light emitting material on the substrate. It may therefore be more suitable to apply the light emitting material on the surface of the substrate, or embed it in the surface of the substrate. As described above, the light emitting material may be applied to the surface of the substrate by first dissolving in solvent, and then painting, dipping or spraying the solution onto the surface.

The substrates may be joined using any fusing or welding techniques known in the art. The energy sources suitable for welding or fusing include, but are not limited to, thermal and radiant energy sources including laser, infrared, ultraviolet heat sources, microwave, and so forth. The substrates will be heated to a temperature at which either one, or both substrates are transformed, i.e. by melting, from a solid to a liquid state.

Lasers are one form of energy commonly used for such purposes and in particular, $CO_2$ and YAG lasers are used for such purposes. These lasers transfer energy to a substrate in a way that results in a rise in the temperature of the polymeric substrate material. In contrast, some lasers, such as the excimer lasers as described above, do not. The polymeric material may go from a solid to a liquid state and back to a solid state upon removal of the energy source. During these phase transitions, a bond between the substrates forms. The strength and quality of the bond often depends on the temperature at which these phase transitions occurs. Therefore, in this embodiment, the light emitting material will be selected so that its emission spectrum will change at the temperature at which an optimal welded or fused bond occurs. If a fluorescent (lye has been selected, it may stop fluorescing altogether, or its fluorescent emission spectrum may be shifted. In any event, the change in emission reflects a change in the light emitting material which further reflects a change in the polymeric substrate. This all will most likely occur just at or above the melting temperature of the polymeric substrate or substrates. The temperature of the substrates will rise upon application of the laser. In this instance, the light emitting material will be selected such that its emission spectrum will change once the optimal fusing or welding temperature has been reached. This temperature will be just at or above the melting point of at least one of the substrates, and maybe both. The method of the present invention therefore allows the non-destructive observation of the bond site.

In a more specific embodiment, the method of the present invention is used in the manufacture of medical devices where at least one polymeric substrate is welded or fused using thermal, radiant or some other source of energy capable of welding or fusing substrates. This process typically involves a first polymeric substrate, and a second substrate which may be polymeric or metallic in nature. If the second substrate is polymeric, it may be of the same polymeric composition as the first substrate, or it may be of a different polymeric composition. Further, the substrate may be comprised of one polymer, or it may be a blend of two or more polymers. The polymers may be homopolymers, copolymers, terpolymers, and so forth, or some mixture thereof.

The light emitting material used in this process may be used to detect the temperature at which an optimum weld or fuse occurs. This temperature may be just at or slightly above the melting temperature of the polymer(s).

The fluorescent dyes are particularly suitable for rise with the medical devices of the present invention because they impart little or no color to the substrate. This is not a requirement, however, and does not therefore bar the use of other types of light emitting materials. These dyes suitably have an emission spectrum from about 250 nm to about 450 nm, and even more suitably from about 250 nm and about 400 nm, whereas dyes having emission spectra above 500 nm, i.e. the visible range, may impart color, a characteristic which may not be as desirable for a medical device.

The method of the present invention has been found to be particularly useful for inspecting the bond sites in intraluminal medical devices such as catheter assemblies which are extremely diminutive in nature making the bonds very difficult to visually inspect, and may be used for any type of fusing or welding method used in the manufacture of such medical devices including those disclosed in U.S. Pat. No. 4,251,305 (heat sealing), U.S. Pat. No. 5,501,759 (laser radiation), and in copending U.S. patent application Ser. No. 09/654,987 (laser beam) all of which are incorporated herein by reference in their entirety. In catheter device assembly, two tubular structures may be fused or welded together to form a catheter shaft, dilatation balloons may be fused to catheter shafts, hypotubes may be fused to catheter shafts, and so forth. Such applications are further illustrated by FIGS. 1–3 described below. Such figures are intended for exemplary purposes only. Heat shrink tubes (not shown) may also be used in the process of the present invention which are put on before application of the laser to the substrate and removed after laser welding.

In embodiments in which two tubes of a catheter shaft are joined, the tubes may each be formed of the same or different polymeric materials, or one may be formed of metal and one formed of a polymeric material. This type of application may be referred to as shaft to shaft welding or a butt/lap joint. The light emitting material or dye is located at least at the interface of the two tubes. The tubes are welded together. Once the optimum temperature for the welding has been achieved, i.e. at or above the melting temperature of the polymeric tubes, the light emitting material no longer emits radiation, or emits radiation at a different wavelength than prior to welding indicating that the welding may be ceased.

In another embodiment, a catheter balloon is welded onto a catheter shaft. The balloon may be welded onto the catheter shaft at both its proximal and distal tip, or at one only. Catheter balloons typically require different properties than the tubular portions of catheter shafts and therefore the polymeric materials used for catheter balloons are typically different than that used in the shaft. This may therefore require a different temperature for welding. In other respects, the process of welding and detecting satisfactory completion of the welding process remain the same. A more detailed discussion of bonding dilatation members to catheter tubes is discussed in copending U.S. patent application Ser. No. 09/654,987 incorporated herein by reference in its entirety. Laser bonding of balloon catheters is also discussed in U.S. Pat. Nos. 5,501,759 and in 5,267,959 both of which are incorporated by reference herein in their entirety.

Another application in which the method of the present invention finds utility is for "cone shaping". This application, in contrast to the welding applications described above, involves only a single substrate of a catheter device, i.e. the dilatation balloon. The light emitting material is used as an indicator of whether or not energy, i.e. a heat source in this instance, has been applied, as well as whether or not adequate energy has been applied.

Figure 2A:
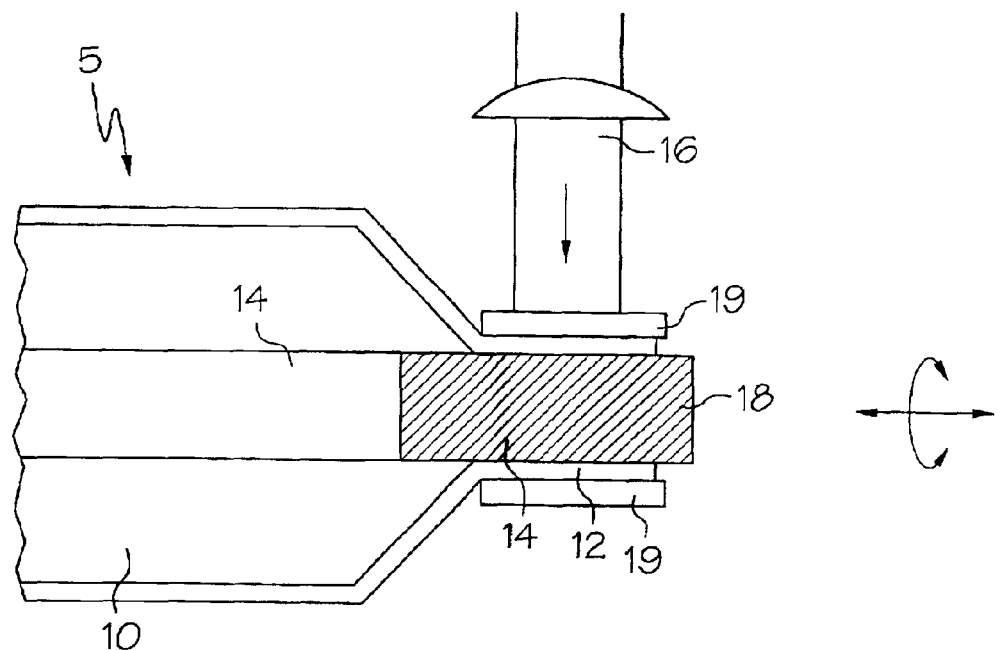
FIGS. 2A and 2B show an alternative embodiment of FIGS. 1A and 1B.
Figure 2B:
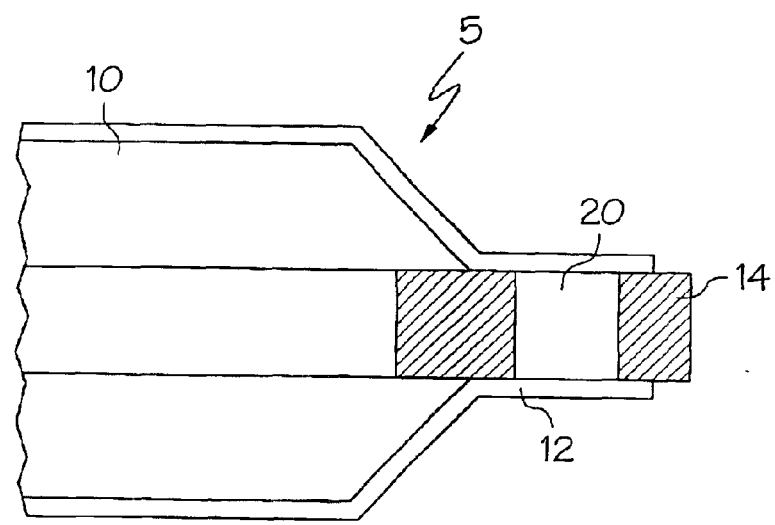
Figure 3A:
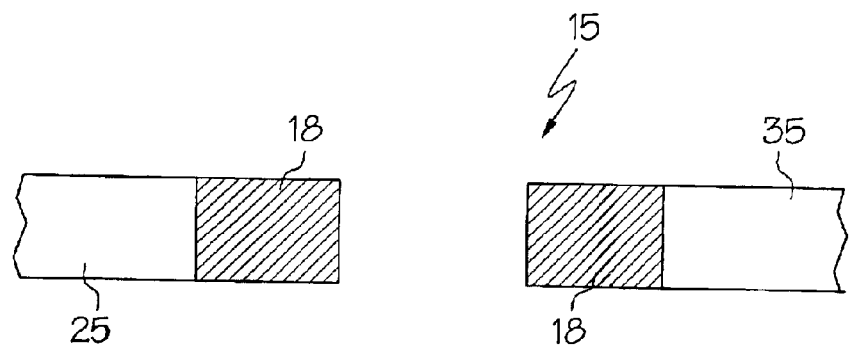
FIGS. 3A, 3B and 3C illustrate a process in which polymeric tubes with the marker coatings of the present invention are joined.
Figure 3B:
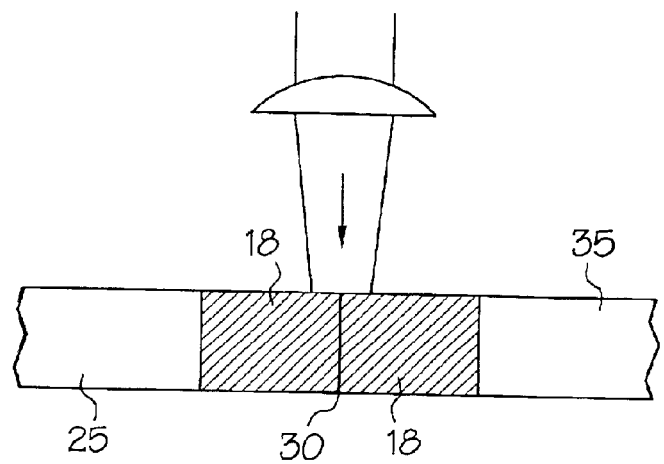
Figure 3C:
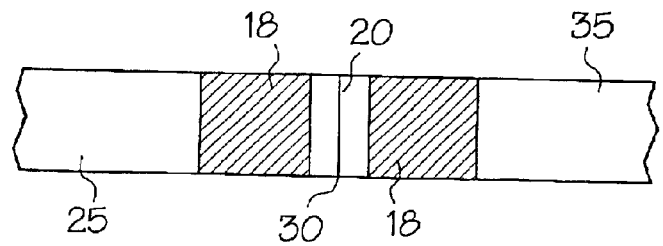
Figure 4A:
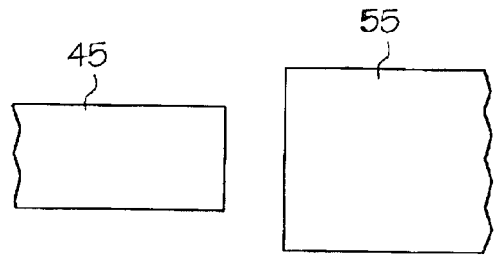
FIGS. 4A–4D illustrate a process wherein a metal catheter shaft having the marker coating of the present invention is joined with a polymeric tube.
Figure 4B:
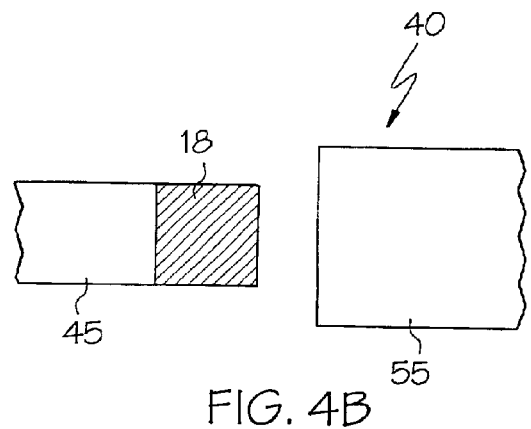
Figure 4C:
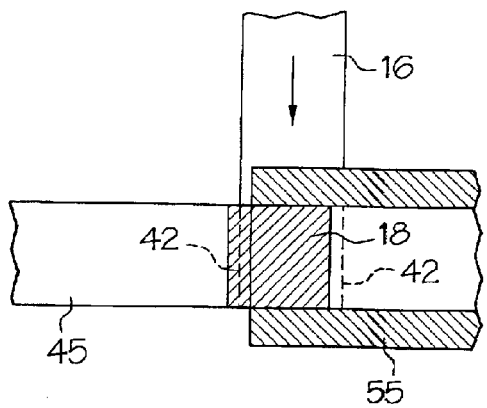
Figure 4D:
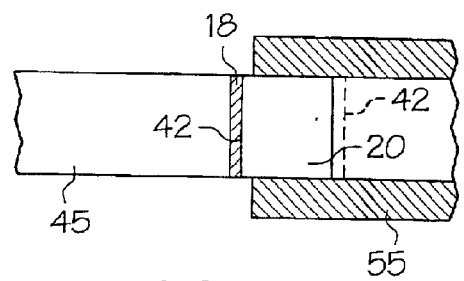
Figure 5A:
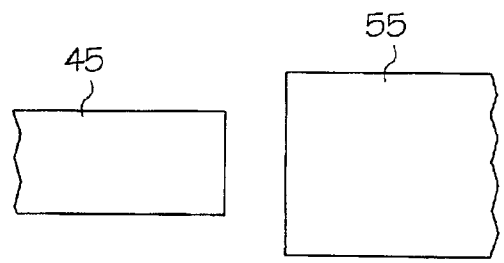
FIGS. 5A–5D illustrate an alternative embodiment of FIGS. 4A–4D.
Figure 5B:
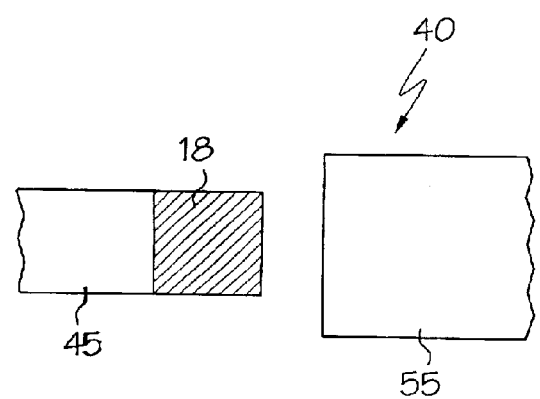
Figure 5C:
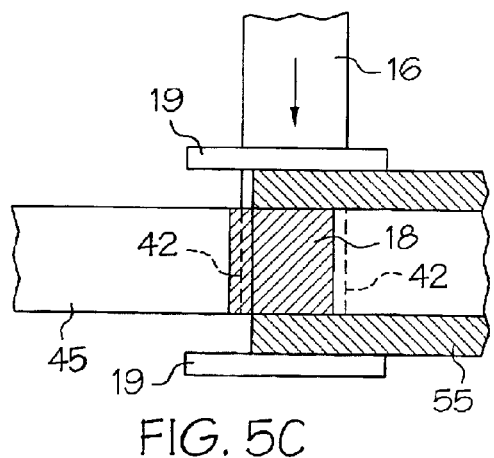
Figure 5D:
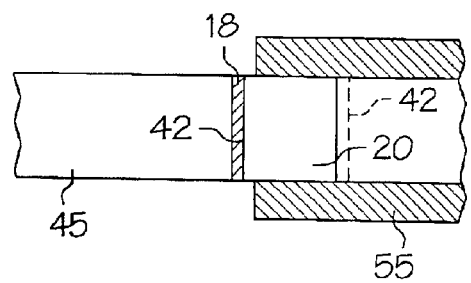

Some embodiments of the present invention are further illustrated by FIGS. 1–3. The following descriptions are exemplary of the invention only, and are not intended to limit the scope of the invention.

Figure 1B:
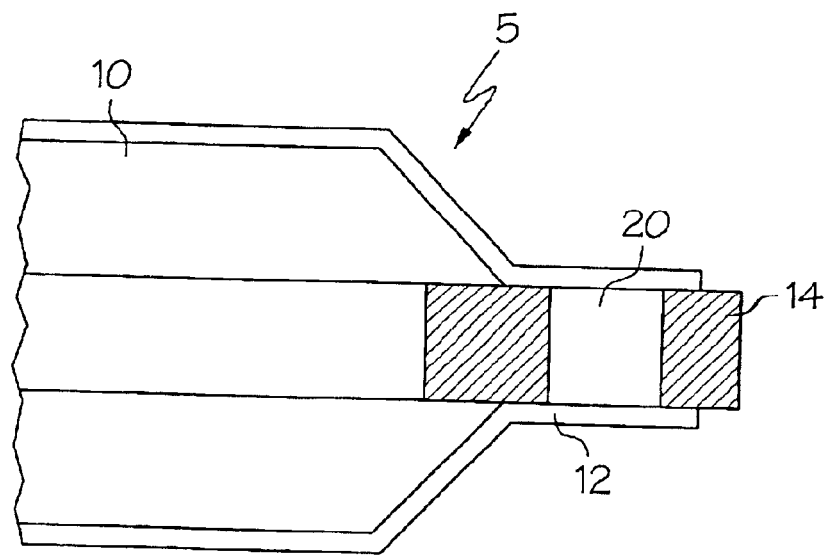

FIGS. 1A and 1B illustrate generally at 5, a dilatation balloon 10 of a catheter device mounted on catheter shaft 14. Dilatation balloon 10 is mounted on catheter shaft 14 at either a proximal or distal tip 12 of balloon 10. A laser beam 16 is applied to the area where the tip 12 of balloon 10 and catheter shaft 14 are desirably welded together. Catheter shaft 14 comprises marker composition 18 indicated on part A of FIG. 1 by the shaded area on catheter shaft 14.

After application of the laser beam 16, and once the temperature for adequate welding has been reached, the marker composition changes color or emission spectra as indicated by the unshaded area 20 in part B of FIG. 1. It will be appreciated that in some circumstances the wall of the distal tip of the balloon and the wall of the catheter shaft 14 may fuse such that a clear demarcation between the individual components is lost.

FIGS. 2A and 2B illustrate an alternative embodiment to that shown in FIG. 1 wherein a cross-section of heat shrink tubing 19 is shown in 1A surrounding catheter shaft 14. The heat shrink tubing 19 absorbs some of the energy from the laser beam 16 and shrinks once a certain amount of energy has been absorbed further constricting the catheter shaft 14 which it surrounds. The heat shrink tubing 19 may be removed.

FIG. 3 illustrates generally at 15 two polymeric tubes, 25 and 35 (each of which has a marker coating represented by the shaded area 18 of the present invention), which are first shown as separate structures in FIG. 3, part A and are joined by welding at an interface 30, in FIG. 3, parts B and C. A laser beam 16 is applied at an area marked by boundaries 32 surrounding the interface 30. The area marked by boundaries 32 in FIG. 3, part C, represented by 20, is the area at which a temperature satisfactory for achieving a good weld has been reached, and at which the indicator dye, for instance, changes color.

FIG. 4 illustrates generally at 40 a metal catheter shaft 45 having the marker coating 18 of the present invention represented by the shaded area, and a polymeric tube 55 both before joining shaft 45 and tube 55, FIG. 3 parts A and B, and after joining shaft 45 and tube 55, FIG. 3 parts C and D. Laser beam 16 is applied to an area marked by boundaries 42. After application of laser beam 16 and once the desired temperature has been reached, marker coating 18 changes color or emission spectra as indicated at 20 which is defined by borders 42.

It will be appreciated that in some alternative embodiments, a heat shrink tube 19 can be used during joining the metal shaft 45 and the polymeric tube 55 as shown in FIGS. 5A–5D. As described above, heat shrink tube 19 surrounds polymeric tube 55. The heat shrink tubing absorbs some of the energy from the laser beam 16 and shrinks thus applying pressure to the polymeric tube 55 further constricting the tube.

Materials particularly useful in the formation of dilatation balloons include, but are not limited to, PET (polyethylene terephthalate); polyolefins such as polyethylene and polypropylene for instance; polyvinyl chloride; SURLYN® polyethylene ionomer copolymer; PEBAX® polyether-block-amide copolymers available from ATOFINA Chemicals, Inc. in Philadelphia, Pa.; PBT (polybutylene terephthalate); poly(butylene terephthalate)-block-poly (tetramethylene oxide); ARNITEL® copolyetherester based on polybutylene terephthalate (PBT)/PTMO; HYTREL® polyester elastomer; polyetherether ketone (PEEK); TEFLON® polytetrafluoroethylene (PTFE), nylon (for example, nylon 12), and their copolymers as well as other polyolefins and silicone elastomers.

Other suitable balloon materials are disclosed in PCT publication WO 97/32624 and commonly assigned U.S. application Ser. No. 08/926,905. Of course, the material should be biocompatible.

Other materials suitable for making both catheters and balloons are discussed in U.S. Pat. No. 6,013,728 to Chen et al. incorporated by reference herein in its entirety.

The interface between the substrates or components to be welded is coated with the light emitting material, a fluorescent dye for instance, or the light emitting material may be embedded into the substrate material itself. Embedding the light emitting material in a substrate may be accomplished immediately after extrusion of the polymeric substrate. The coating may be located on the surface of one or both substrates, may be embedded right in one or in both substrates, or may be blended in the polymeric composition prior to formation of the polymeric device.

As described above, the substrates of the medical device may be fused or welded together by thermal or radiant sources of energy, suitably a laser, for instance. In order to achieve an optimal bond, certain temperatures must be met or exceeded.

In one embodiment of the present invention, the welding device is a laser. Desirably, the laser is a carbon dioxide ($CO_2$) laser operating in the infrared region, and even more desirably, the laser operates at a wavelength of about 10.6 microns.

The laser will be selected based on the polymeric materials that are utilized in the manufacture of the article concerned. The laser is "matched" to the polymeric material selected. Different polymeric materials have different absorptivity with respect to the wavelength of the energy available. For instance, HYTREL® polyesters and PET will absorb energy quite sufficiently in the infrared region of about 10.6 microns. However, polyethylene and polypropylene, absorb energy effectively at a wavelength of about 3.4 microns. For more information on absorbtivity, see *The Infrared Spectra Atlas of Monomers and Polymers*, published by Sadtler Research Laboratories.

More on this topic can be found in U.S. Pat. No. 5,501,759 and in U.S. Pat. No. 5,267,959 both of which are incorporated by reference herein in their entirety.

In general, polymeric materials do not absorb energy uniformly, but rather exhibit bands of markedly increased absorptivity. As polymers become more complex, so do their energy absorption spectra. Polyesters exhibit a band of absorption ranging from about 7–11 microns, a range that encompasses the 10.6 micron wavelength.

The tendency in polymers to exhibit wavelength-selective absorption is observed not only in connection with infrared energy, but throughout the electromagnetic spectrum.

A commonly used range for the laser energy density or irradiance for welding is typically less than about 5 watts/$cm^2$, and more likely in the range of about 0.5–2 watts/$cm^2$.

The laser means may also operate in the UV-vis range. For instance, in this case, the laser means may generate a beam of laser energy at a wavelength of approximately 500 nm to 850 nm.

Other suitable lasers include diode lasers. For instance, a GaAlAs diode laser may be utilized which emits a beam of laser energy at a wavelength of approximately 780 nm to 820 nm. Other suitable diode lasers include GaAs (infrared) and GaAs:Si (infrared).

In another embodiment of the present invention, the welding device is a radio frequency or RF heating device.

Suitably, for medical devices, the light emitting material is a fluorescing agent which imparts little or no color to the device. Upon irradiation with UV light or e-beam radiation, the fluorescent dye fluoresces at a specified applied wavelength indicating its presence and location.

The fluorescing agent is selected to that its emission spectrum will undergo a change upon application of the selected energy source. This change in emission may be a shift in its fluorescent spectrum, or it may be a nonfluorescent emission upon achieving the temperature required for optimal bonding.

The temperature at which the emission spectrum of the light emitting material changes is suitably just at or above, the melting temperature of the polymer. Therefore, it is necessary to match the temperature of the polymeric material and the light emitting material.

For instance, thermoplastic polyurethanes and polyether-block-amide copolymers melt above about 425° F. (about 220° C.). Therefore, the light emitting agent would be selected so as to exhibit a change in emission at temperatures of about 425° F. (about 220° C.) or higher. However, the temperature of change cannot be too much higher because if the polymeric material becomes too molten the bond line may be distorted and imperfections may be present.

The light emitting material, suitably a fluorescent compound in this instance, is exposed to UV light such that only the unexposed light emitting material illuminates providing a definitive area of welding. In other words, the light emitting material may cover a wider area than that which will be welded. The welded area will exhibit a different emission, but the area around the weld will continue to fluoresce forming a border around and thereby clearly delineating the welded area.

Either the device which is used for detecting the radiation emitted from the light emitting material, or the welding device itself, may be equipped with an alarm system that will terminate operation of the laser, for instance, or other welding means once the device no longer detects emitted radiation, or the spectrum of emitted radiation has changed. For instance, the device will detect when a fluorescent dye no longer fluoresces, or its spectrum of emission has changed.

The above embodiments are intended to exemplify and illustrate the general principles of the invention. One of skill in the art would understand that there are various modifications that can be made to the invention without deviating from the scope of the invention. The above described embodiments are therefore not intended to limit the scope of the invention in any way.

What is claimed is:

1. A method of manufacturing a medical device, comprising the steps of:
   a) providing a first polymeric medical device substrate part and a second medical device substrate part to be joined;
   b) selecting a light emitting material having a first emission spectrum and which, upon exposure to a predetermined energy dosage, provides a second emission spectrum different from said first emission spectrum or a non-emission;
   c) applying said light emitting material to said polymeric substrate at a location where the first substrate and second substrate will be joined; and
   d) applying the predetermined energy source to said substrate sufficient to change said first emission spectrum of said light emitting material to said second emission spectrum or to a non-emission and sufficient to join the first and second parts.

2. The method of claim 1 further comprising the step of e) detecting said second emission spectrum on said polymeric substrate.

3. The method of claim 1 wherein said light emitting material has a first emission spectrum and a non-emission upon exposure to a predetermined energy dosage.

4. The method of claim 2 further comprising the step of f) utilizing said detected emission spectrum as an indicator of the receipt by the substrate of said predetermined energy dosage.

5. The method of claim 1 further comprising the step of joining said first polymeric substrate to a second polymeric substrate before applying said predetermined energy source.

6. The method of claim 1 wherein said first and said second emission spectrum is selected from visible, fluorescent and phosphorescent emissions.

7. The method of claim 1 wherein said light emitting material has first emission spectrum from about 200 nm to about 800 nm.

8. The method of claim 1 wherein said light emitting material has a first emission spectrum from about 250 nm to about 450 nm.

9. The method of claim 1 wherein said energy source is selected from thermal, radio frequency, ultraviolet, laser, ultrasound, gamma radiation, and ion beam.

10. The method of claim 1 wherein said energy source is thermal or is a laser.

11. The method of claim 1 wherein said energy source is provided at a wavelength of about 2 to about 12 microns.

12. The method of claim 1 wherein said energy source is provided at a wavelength of about 200 to about 800 nm.

13. The method of claim 12 wherein said light emitting material is a fluorescent dye.

14. The method of claim 13 wherein said light emitting material has a first emission spectrum from about 250 to about 450 nm.

* * * * *